(12) United States Patent
Teramoto et al.

(10) Patent No.: US 9,248,474 B2
(45) Date of Patent: Feb. 2, 2016

(54) GENERATION DEVICE, GENERATION METHOD, ANTIBODY CHIP, COMPUTER PROGRAM AND NON-TRANSITORY COMPUTER-READABLE MEDIUM

(75) Inventors: Youichi Teramoto, Omuta (JP);
Kazuhira Sakamoto, Omuta (JP);
Toshikazu Kawaguchi, Sapporo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 205 days.

(21) Appl. No.: 13/704,493

(22) PCT Filed: Jun. 10, 2011

(86) PCT No.: PCT/JP2011/063404
§ 371 (c)(1),
(2), (4) Date: Dec. 14, 2012

(87) PCT Pub. No.: WO2011/158759
PCT Pub. Date: Dec. 22, 2011

(65) Prior Publication Data
US 2013/0089467 A1    Apr. 11, 2013

(30) Foreign Application Priority Data
Jun. 16, 2010    (JP) .................................. 2010-136771

(51) Int. Cl.
*B05D 7/24*    (2006.01)
*G01N 33/50*    (2006.01)
(Continued)

(52) U.S. Cl.
CPC ................ *B05D 7/227* (2013.01); *C07K 16/00* (2013.01); *G01N 33/50* (2013.01); *G01N 33/54366* (2013.01)

(58) Field of Classification Search
CPC .......... G01N 33/50; B05D 7/24; B05D 7/227
USPC ................ 422/501, 504, 509, 514, 515, 521, 422/63–68.1
See application file for complete search history.

(56) References Cited

U.S. PATENT DOCUMENTS 4,025,311 A *   5/1977   Bochinski ....................... 422/67
6,083,763 A     7/2000   Balch
(Continued)

FOREIGN PATENT DOCUMENTS

AU    6646398 A    7/1998
CN    101038287 A   9/2007
(Continued)

OTHER PUBLICATIONS

International Search Report, International Application No. PCT/JP2011/063404, mailed Sep. 6, 2011, 4 pages.
(Continued)

*Primary Examiner* — Brian R Gordon
(74) *Attorney, Agent, or Firm* — Rankin, Hill & Clark LLP

(57) ABSTRACT

A generation device and the like for generating long-life antibody chips which can be produced and held in stock is a generation device and the like for generating an antibody chip by binding antibody to a cup, including an antibody solution holder that holds antibody solution having antibody, a buffer solution holder that holds buffer solution, and an injector that injects solution into the cup. The injector has an inlet out of which solution is injected. The injector injects the buffer solution held by the buffer solution holder. The injector injects the antibody solution held by the antibody solution holder with the inlet in the buffer solution in the cup.

4 Claims, 10 Drawing Sheets

(51) Int. Cl.
*B05D 7/22* (2006.01)
*C07K 16/00* (2006.01)
*G01N 33/543* (2006.01)

(56) References Cited

U.S. PATENT DOCUMENTS

| | | | |
|---|---|---|---|
| 6,203,759 B1 * | 3/2001 | Pelc et al. | 422/521 |
| 6,312,960 B1 | 11/2001 | Balch et al. | |
| 6,331,441 B1 | 12/2001 | Balch et al. | |
| 6,479,301 B1 | 11/2002 | Balch et al. | |
| 6,592,825 B2 * | 7/2003 | Pelc et al. | 422/521 |
| 6,803,238 B1 | 10/2004 | Eggers | |
| 8,313,711 B2 * | 11/2012 | Brown et al. | 422/501 |
| 2001/0016177 A1 * | 8/2001 | Pelc et al. | 422/100 |
| 2001/0053334 A1 | 12/2001 | Chen et al. | |
| 2001/0055801 A1 | 12/2001 | Chen et al. | |
| 2002/0028160 A1 | 3/2002 | Xiao et al. | |
| 2002/0051979 A1 | 5/2002 | Chen et al. | |
| 2002/0164824 A1 | 11/2002 | Xiao et al. | |
| 2003/0087309 A1 | 5/2003 | Chen | |
| 2003/0143725 A1 | 7/2003 | Chen et al. | |
| 2004/0014102 A1 | 1/2004 | Chen et al. | |
| 2004/0023249 A1 | 2/2004 | Balch | |
| 2007/0218545 A1 | 9/2007 | Uematsu et al. | |
| 2008/0227126 A1 | 9/2008 | Uematsu et al. | |
| 2009/0239759 A1 | 9/2009 | Balch | |

FOREIGN PATENT DOCUMENTS

| | | | |
|---|---|---|---|
| EP | 990142 A | 4/2000 | |
| EP | 1249705 A2 | 10/2002 | |
| EP | 1257354 A | 11/2002 | |
| EP | 1257355 A | 11/2002 | |
| EP | 2295988 A2 | 3/2011 | |
| JP | 62-261065 A | 11/1987 | |
| JP | 2002-267666 A | 9/2002 | |
| JP | 2003-107097 A | 4/2003 | |
| JP | 2003-529056 A | 9/2003 | |
| JP | 2004-502923 A | 1/2004 | |
| JP | 2005-099011 A | 4/2005 | |
| JP | 2007-017252 A | 1/2007 | |
| JP | 2007-248361 A | 9/2007 | |
| JP | 2008-224524 A | 9/2008 | |
| JP | 2009-2956 A | 1/2009 | |
| JP | 2009-156767 A | 7/2009 | |
| JP | 2010-78605 A | 4/2010 | |
| WO | 98/29736 A1 | 7/1998 | |
| WO | 01/62377 A2 | 8/2001 | |
| WO | 01/62378 A | 8/2001 | |

OTHER PUBLICATIONS

English Abstract of JP 2003-529056, 2 pages.
English Abstract of JP 2004-502923, 2 pages.
English Abstract of EP 1257355, 2 pages.
English Abstract of EP 1257354 (abstract of corresponding WO 01/62377), 2 pages.
English Abstract of JP 2003-107097, 2 pages.
English Abstract of JP 2010-78605, 2 pages.
English Abstract of EP 990142 (abstract of corresponding WO 9829736), 2 pages.
English Abstract of JP 2009-2956, 2 pages.
English Abstract of JP 2008-224524, 2 pages.
English Abstract of JP 2007-248361, 2 pages.
English Abstract of CN 101038287, 2 pages.

* cited by examiner

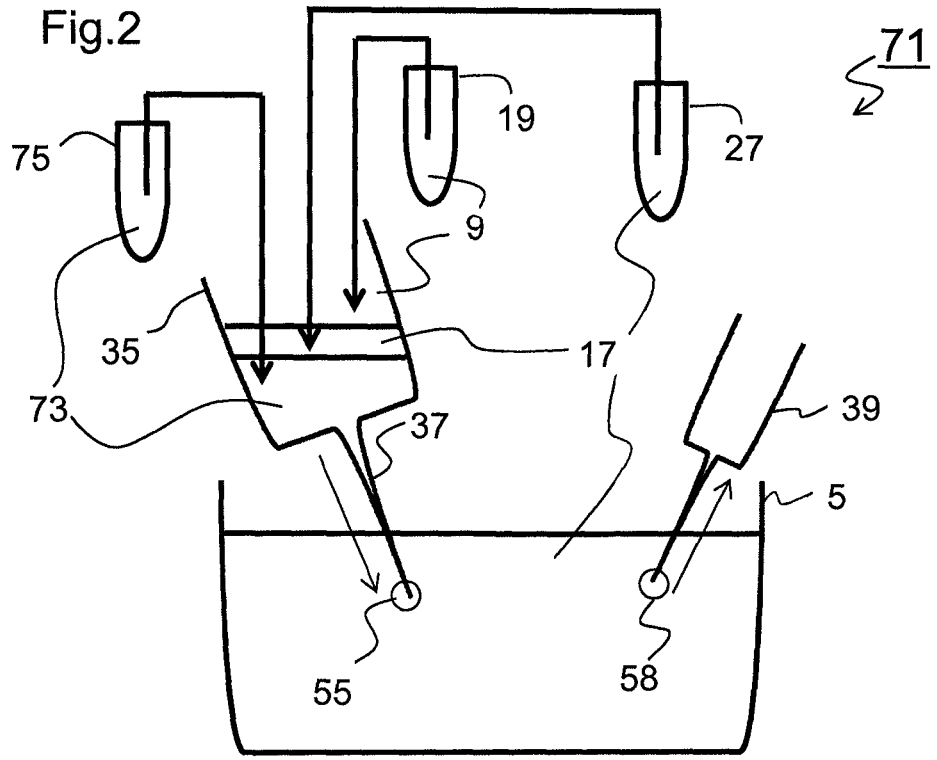
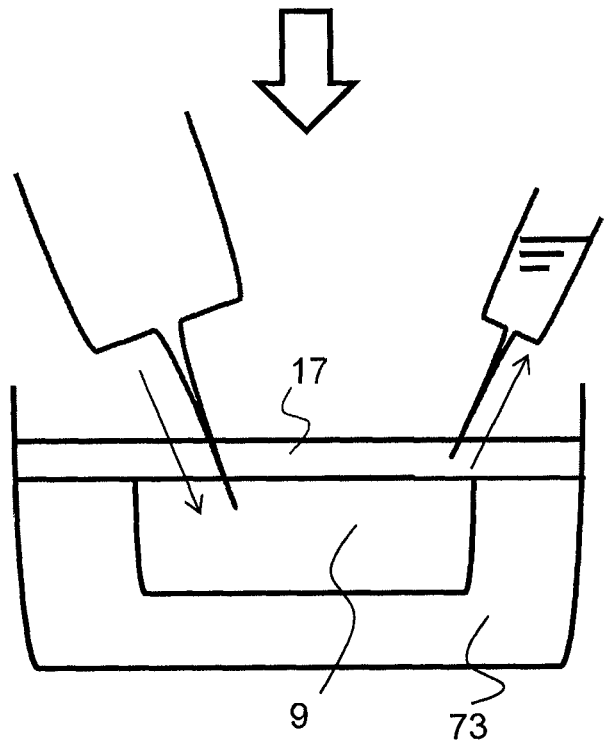
Fig.2

Fig.8
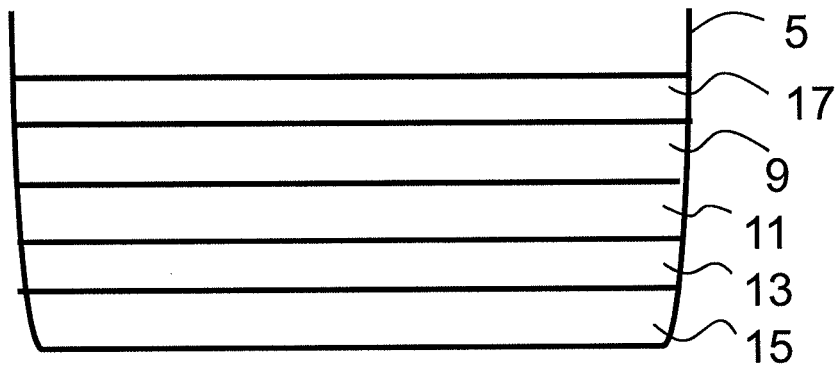
(a)
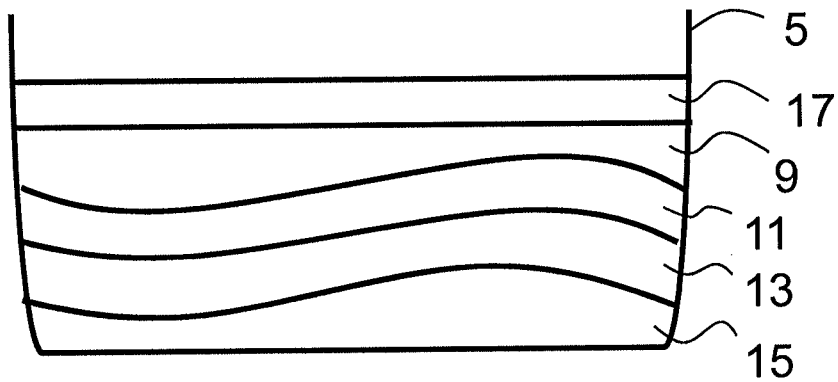
(b)
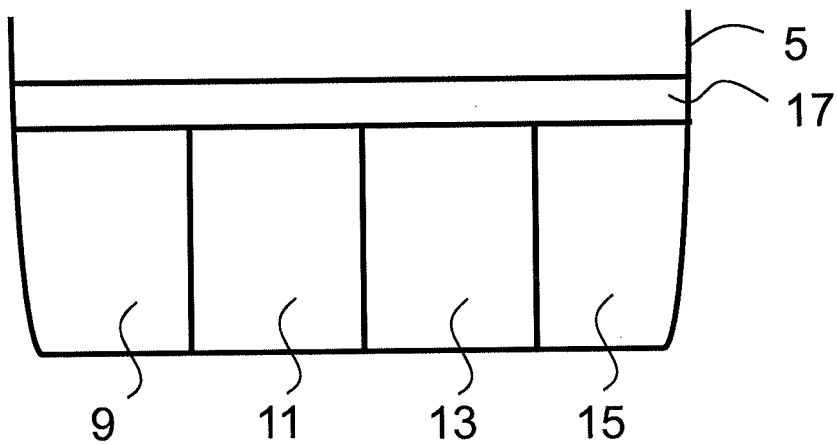
(c)

GENERATION DEVICE, GENERATION METHOD, ANTIBODY CHIP, COMPUTER PROGRAM AND NON-TRANSITORY COMPUTER-READABLE MEDIUM

TECHNICAL FIELD

The present invention relates to a generation device, generation method, an antibody chip, a computer program, and a non-transitory computer-readable medium, and particularly relates to a generation device and the like for generating an antibody chip by binding antibody to a cup.

BACKGROUND ART

Antibody chips in which antibody is immobilized are utilized for detecting infection such as hepatitis C and the flu, or environmental pollutant in food. (Refer to Patent Literature 1, for example.) For example, by utilizing antibody chips, it is possible to determine rapidly whether the flu is H1N1, Hong Kong type, a new type, or the like.

As an antibody chip, a microplate with a plurality of cups in which antibody is immobilized is generally used. If a specimen to be examined has an antigen, the antigen brings about an antigen antibody reaction with the antibody immobilized in the cup and the specimen is determined as positive by the examination.

Referring to FIG. 9, a cup 105 of a conventional antibody chip in which antibody is immobilized will be described. FIG. 9 illustrates a cross-section view of the cup 105 of a conventional antibody chip. Generally, antibody cannot be bound directly to a plastic cup 105. Thus, antibody has been immobilized in the cup 105 by stacking activation layer 115, immobilization layer 113, coupling layer 111 and antibody layer 109 successively to the cup 105.

CITATIONList

Patent Literature

[Patent Literature 1]: JP 2005-99011 A.

SUMMARY OF INVENTION

Technical Problem

However, conventional antibody chips have been generated through a plurality of procedures which take a long time, as described below. Referring to FIG. 10, an outline of a conventional generation process of antibody chips is described.

First, activation solution that forms activation layer 115 is injected into a cup 105 (step ST101). After placing the cup for 2-3 hours, the activation solution is bound to the cup 105 to form the activation layer 115 (step ST102). The cup 105 is washed to remove excess activation solution (step ST103). Subsequently, immobilization solution that forms immobilization layer 113 is injected into the cup 105 (step 104). After placing the cup for 1-2 hours, the immobilization layer 113 is formed on the activation layer 115 (step ST105). The cup 105 is washed to remove excess immobilization solution (step ST106). Next, a coupling solution that forms coupling layer 111 is injected into the cup 105 (step ST107). After placing the cup for 1-2 hours, the coupling layer 111 is formed on the immobilization layer 113 (step ST108). The cup 105 is washed to remove excess coupling solution (step ST109). Further, antibody solution that forms antibody layer 109 is injected into the cup 105 (step ST110). Finally, buffer solution that forms a buffer layer 117 is injected into the cup 105 (step ST111). After placing the cup for 1 day or so, antibody is bound to the coupling layer 111 and an antibody chip is completed (step ST112).

It has taken 2-3 days for the conventional process as a whole to generate an antibody chip. Further, antibody and so on has been exposed to air because the volume of a cup is generally as small as 30 μL, and solution has been injected into such small cups by handwork and through a multistep process. As a result, air 119 is contained between the antibody solution layer 113 and the buffer solution layer 117, drastically limiting the life-span of the antibody chip to as short as 1 week or so.

As described above, because antibody chips have short life-span, the antibody chips cannot be produced and held in stock. As a result, even in emergencies such as poisoning examination or infection examination, inspection agencies had to take time to ask a trustee company to generate antibody chips, which prevented a speedy examination.

It is, therefore, an object of the present invention to provide a generation device and the like for generating long-life antibody chips which can be produced and held in stock.

Solution to Problem

A first aspect in accordance with the present invention provides a generation device for generating an antibody chip by binding antibody to a cup, comprising a buffer solution holder that holds buffer solution, an antibody solution holder that holds antibody solution having the antibody, and a solution adjuster that adjusts solution in the cup, wherein the solution adjuster includes an injector that injects solution into the cup out of an inlet, and the injector injects the antibody solution with the inlet in the buffer solution injected into the cup.

A second aspect in accordance with the present invention provides the generation device of the first aspect, further comprising a bond solution holder that holds bond solution for binding the antibody and the cup, and an infusion holder that holds the antibody solution and the bond solution with the antibody solution and the bond solution in isolation by the buffer solution, wherein the injector injects the antibody solution, the buffer solution and the bond solution held by the infusion holder with the inlet in the buffer solution in the cup.

A third aspect in accordance with the present invention provides the generation device of the second aspect, wherein the infusion holder holds the bond solution, the buffer solution and the antibody solution in ascending order according to distance to the inlet, and the injector injects the bond solution, the buffer solution and the antibody solution into the cup so that layers of the bond solution and the antibody solution are formed in order of injection in the cup.

A fourth aspect in accordance with the present invention provides the generation device of the first aspect, wherein the solution adjuster further includes an ejector that ejects the buffer solution in the cup out of an outlet, and the ejector ejects the buffer solution in accordance with injection of the solution by the injector.

A fifth aspect in accordance with the present invention provides the generation device of the fourth aspect, wherein the solution is injected into a plurality of cups, and the injector injects the solution at the same time into a part of or all of the plurality of cups.

A sixth aspect in accordance with the present invention provides the generation device of the fifth aspect, wherein the solution adjuster further includes a sealing unit that seals the cup keeping a path of injection of the solution by the injector and a path of ejection of the buffer solution by the ejector, the injector includes a plurality of inlets in accordance with the plurality of cups, the ejector includes a plurality of outlets in accordance with the plurality of cups, and the injector injects the antibody solution while each of the plurality of inlets and the plurality of outlets are inside of each of the plurality of cups and while each of the plurality of inlets is positioned lower than each of the plurality of outlets.

A seventh aspect in accordance with the present invention provides the generation device of the sixth aspect, wherein the injector injects the solution at the same time into an even number of the cups, a flow path to each of the inlets is biforked twice or more to the number of the cups, and a part of or all of the outlets of the cups into which the injector injects solution at the same time are positioned on the same level.

An eighth aspect in accordance with the present invention provides the generation device of the second aspect, further comprising a transportation unit that transports the antibody solution from the antibody solution holder to the injector, wherein the transportation unit includes a valve selector that controls inflow of the antibody solution to a flow path through which the antibody solution is transported, and the valve selector includes a solenoid valve that switches a valve by energization and keeps a switching condition without the energization.

A ninth aspect in accordance with the present invention provides the generation device of the eighth aspect, further comprising a driver circuit that drives the solenoid valve, wherein the driver circuit includes a solenoid that activates the solenoid valve by energization, a capacitor that stores charge by beginning of the energization, a relay that switches connection relation, and a switch unit that controls switching the connection relation by the relay, the solenoid, the capacitor and the relay are sequentially connected, the switch unit is connected in parallel with the solenoid, the capacitor and the relay, the relay permits the energization to the solenoid at beginning of applying voltage parallel to the switch unit, and the relay switches the connection relation at stopping of the applying voltage so that the solenoid, the capacitor and the relay forms a closed circuit which does not include the switch unit.

A tenth aspect in accordance with the present invention provides a generation method for generating an antibody chip by binding antibody to a cup, comprising a buffer solution injection step of injecting buffer solution into the cup, and a function solution injection step of injecting an antibody solution including the antibody into the cup with an inlet in the buffer solution injected into the cup.

An eleventh aspect in accordance with the present invention provides the generation method of the tenth aspect, wherein, in the function solution injection step, bond solution for binding the antibody and the cup is injected into the cup before injection of the antibody solution, with the bond solution and the antibody solution in isolation by the buffer solution, so that, in the cup, a layer of the bond solution is made between the layer of the antibody solution and the cup.

A twelfth aspect in accordance with the present invention provides the generation method of the tenth aspect, wherein, in the function solution injection step, the buffer solution is ejected in accordance with injection of solution into the cup.

A thirteenth aspect in accordance with the present invention provides an antibody chip comprising a cup to which antibody is bound, wherein the antibody is injected and bound to the cup without exposure to air by injecting antibody solution including the antibody with an inlet in buffer solution injected into the cup.

A fourteenth aspect in accordance with the present invention provides a computer program capable of causing a computer that controls an injector that injects solution into a cup to execute the generation method of the tenth aspect.

A fifteenth aspect in accordance with the present invention provides a non-transitory computer-readable medium storing the computer program of the fourteenth aspect.

The ejector can eject buffer solution from a cup by, for example, ejecting buffer solution at the same time with injecting solution into the cup or ejecting buffer solution by the same amount with that of injection of solution before or after the injection, only if buffer solution does not overflow from the cup. Here, the ejector includes an active ejector such as an aspirator that aspirates buffer solution in the cup or a passive ejector composed of only an outlet and a flow path, for example.

In addition, the shapes of a plurality of cups can be different one another and the heights of the outlets above the bottoms of the plurality of cups can be positioned differently, only if, when an injector injects the same amount of solution into each of a plurality of cups, the same amount of buffer solution is ejected out of each of the plurality of cups by an ejector. The outlets may be positioned on the same level above the bottoms of the cups when, for example, the cups to which solution is injected at the same time are the same in shape. Similarly, the inlets in a plurality of cups may be positioned on the same level above the bottoms of the cups.

Further, the number of cups to which an injector injects solution at the same time maybe $2^N \times P$, where N and P are natural numbers. Then, a flow path from an infusion holder to inlets may be divided into P branches and biforked N times. Further, it is favorable to be configured so that the distance between an infusion holder and each of the cups is the same. For example, a flow path may be biforked N times such that a part of or all the path from the infusion holder to the inlets has a fractal structure.

Further, the transportation unit may transport not only the antibody solution, but also the buffer solution from the buffer solution holder to the injector, the bond solution from the bond solution holder to the injector, and so on.

Further, apart from the antibody chip generated as a product, antibody may be bound to one or more cups in order to evaluate the quality, for example. Then, the cups to be evaluated may not be necessarily injected and generated at the same time as the antibody chip as a product is injected and generated.

Further, the switch unit may be a magnet coil. Further, the relay may include three contact points, wherein the first contact point is connected to the capacitor, the second contact point is connected to the solenoid and the switch unit, the third contact point is connected to the switch unit, one end of the capacitor is connected to the first contact point of the relay, the other end of the capacitor is connected to the solenoid, one end of the solenoid is connected to the capacitor, the other end of the solenoid is connected to the second contact point of the relay and the switch unit, one end of the switch unit is connected to the second contact point of the relay and the solenoid, the other end of the switch unit is connected to the third contact point of the relay, the relay connects the first contact point and the third contact point to start the energization to the solenoid, and, when the energization is stopped, the relay connects the first contact point and the second contact point to form the closed circuit.

Advantageous Effects of Invention

According to each aspect of the present invention, it is possible to generate an antibody chip without exposure to air by injecting antibody solution with an inlet in buffer solution injected into a cup. Therefore, a long-life antibody chip can be generated. As a result, antibody chips can be produced and held in stock. Accordingly, rapid examination can be performed when necessary.

In particular, according to any of the first through ninth aspects of the present invention, a generation device by which antibody chips are generated automatically may be provided. Therefore, antibody chips can be easily generated more rapidly, more accurately and in larger amounts.

In addition, according to the second or the eleventh aspect of the present invention, an antibody chip can be generated without exposure of not only antibody solution but also bond solution to air. Therefore, antibody can be kept from air more surely, resulting in longer-life antibody chips. In particular, according to the second aspect, antibody solution and bond solution can be injected to a cup at a time by holding antibody solution and bond solution in an infusion holder with the antibody solution and the bond solution in isolation by buffer solution. Then, the time and cost for generating antibody chips can be decreased because placement procedures and washing procedures are unnecessary in the generation process of antibody chips.

Further, according to the third or eleventh aspect of the present invention, an antibody chip which has an antibody solution layer and a bond solution layer in an intended order can be generated by injecting the bond solution and the antibody solution in a predetermined order.

Further, according to the fourth or twelfth aspect of the present invention, the buffer solution can be ejected while antibody solution and so on are injected. Therefore, an antibody chip can be generated without overflow of buffer solution even when antibody solution and so on is injected into a cup filled with buffer solution. Further, according to the fifth aspect of the present invention, an antibody chip which has a plurality of cups densely packed on a microplate can be generated in a short time.

Further, according to the sixth aspect of the present invention, a sealing unit seals each cup keeping a path of injection of solution by the injector and a path of ejection of the buffer solution by the ejector. By this, it is easier to generate an antibody chip without exposure of solution in a cup to air. In particular, it is easier to generate a long-life antibody chip by filling a cup with buffer solution in advance to remove air in the cup absolutely.

In addition, according to the sixth aspect of the present invention, it is easier to bind antibody solution and so on to a cup surely because an inlet is positioned lower in the cup than an outlet.

Further, according to the seventh aspect of the present invention, a flow path is biforked in accordance with a plurality of cups. It is essential to inject the same amount of solution into each cup when solution is injected into a plurality of cups at the same time for generating a homogenous antibody chip. However, flow of solution is made complicated around a branching point of a flow path. Thus, it is necessary to devise a way to inject the same amount of solution from one infusion holder out of a plurality of inlets at the same time. Here, if there are only a small number of cups fewer than 10, for example, it is possible to use a standardized branching connector. But, it is impractical to connect such branching connectors one after another (like an electrical multiple-tap) for a large number of cups more than 20, for example. This is because the effect of each branching connector on the flow speed in a branched flow path is too much to be neglected and because it is difficult to expect that the same amount of solution is injected into each of a plurality of cups.

Thus, by utilizing the seventh aspect of the present invention, assuming one or a few branching connectors which divide flow paths into less than 10 branches, for example, are adopted, it is effective to divide other branching points using symmetric biforked branching connectors repeatedly. This is because the same amount of solutions can be injected into a lot of cups at the same time while identical environments of the flow paths such as the shape of each flow path, the distance to each of inlets, and so on are maintained.

Further, according to the seventh aspect of the present invention, buffer solution can be equally ejected from every cup because the outlets of the cups are positioned on the same level. Therefore, because the same amount of solution is injected and ejected at the same time at all the cups into which the injector injects solution, it is easier to generate an antibody chip in which antibody is homogeneously bound to a plurality of cups.

Further, according to the eighth aspect of the present invention, it is possible to provide a generation device including a transportation unit that transports solution such as antibody solution automatically. Therefore, it is easier to generate an antibody chip rapidly. Besides, by equipping the transportation unit with a self-sustaining type solenoid valve as a solenoid valve of a valve selector that let solution into a flow path, heat generation from the solenoid valve can be drastically suppressed. Therefore, because antibody can be transported without damage from heat, it is easier to generate a long-life antibody chip.

Further, according to the ninth aspect of the present invention, it is possible to control switching condition of the solenoid valve with a single solenoid. Further, only the switch unit is a necessary component of the circuit as a unit for determining the direction of the current through the solenoid. Therefore, it is possible to control the solenoid valve with a smaller size of control circuit than ever before. Then, heat generation can be suppressed as much as possible. For example, it is possible to provide a solution transportation device which transports a small amount of solution, including a self-sustaining solenoid valve in a small component such as a valve selector. Then, it is possible to transport a small amount of solution without damage, the solution such as antibody solution which is expensive and extremely sensitive to heat, resulting in easier generation of long-life antibody chips.

BRIEF DESCRIPTION OF DRAWINGS

FIG. 2 illustrates a schematic view of a generation device 71 for generating the antibody chip 1 in FIG. 1.

FIG. 8 illustrates the examples of distribution of solutions in the antibody chip 1 in FIG. 1.

DESCRIPTION OF EMBODIMENTS

Referring to the figures, the best mode of the present invention will be described below. Here, the present invention is not limited to the following embodiment.

EXAMPLE

Figure 1:
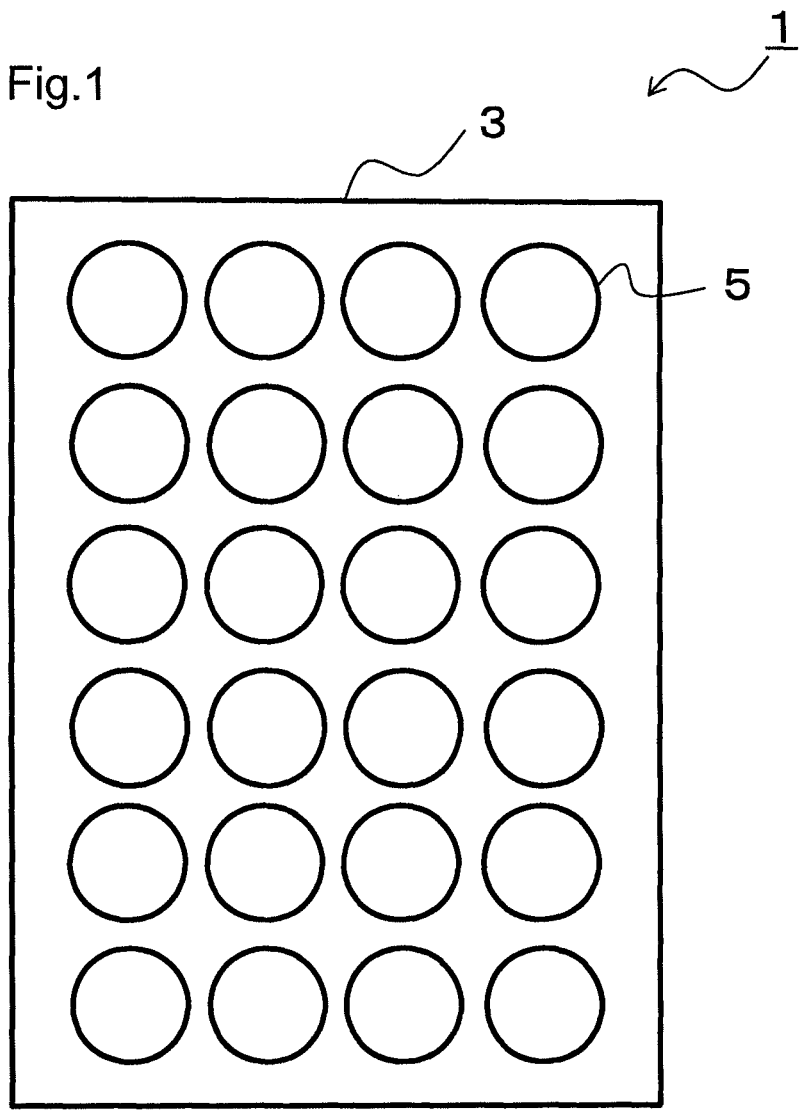
FIG. 1 illustrates a schematic view of an antibody chip 1 in accordance with the present invention.

FIG. 1 illustrates a schematic view of an antibody chip 1 in accordance with the present invention. The antibody chip 1 includes a microplate 3. The microplate 3 includes a cup 5 in which antibody is immobilized.

The brief summary of a generation device of the antibody chip 1 of FIG. 1 is described below. FIG. 2 illustrates a schematic view of a generation device 71 for generating the antibody chip 1 in accordance with the present embodiment.

Generally, antibody cannot be bound directly to the cup 5. Thus, when immobilizing the antibody to the cup 5 of the antibody chip 1, bond solution 73 is utilized to bind antibody to the cup 5.

Referring to FIG. 2, the generation device 71 includes the cup 5 to which antibody is to be bound, an antibody solution holder 19 that holds antibody solution 9 which includes antibody, a bond solution holder 75 that holds bond solution 73, a buffer solution holder 27 that holds buffer solution 17, an infusion holder 35 that holds solution to be injected into the cup 5, an injector 37 that injects solution in the infusion holder 35 into the cup 5, and an ejector 39 that ejects the buffer solution 17 in the cup 5. The injector 37 includes an inlet 55. The ejector 39 includes an outlet 58. The cup 5 is filled with the buffer solution 17 in advance.

The infusion holder 35 holds the bond solution 73, the buffer solution 17, and the antibody solution 9 in the ascending order according to the distance to the inlet 55 with the bond solution 17 and the antibody solution 9 in isolation by the buffer solution 17. Then, the injector 37 injects the bond solution 73, the buffer solution 17 and the antibody solution 9 in this order into the cup 5 with the inlet 55 in the buffer solution 17 in the cup 5, resulting in the antibody chip 1. At this time, the ejector 39 ejects the buffer solution 17 as necessary so that the buffer solution 17 does not overflow out of the cup 5. In addition, the injector 37 injects solution into the cup 5 so as to form layers of the bond solution 73 and the antibody solution 9 in the ascending order according to the distance to the cup 5.

Here, two or more kinds of solution are often used as the bond solution 73. Referring to the FIG. 2, coupling solution 11, immobilization solution 13 and activation solution 15 are used as the bond solution 73 in this embodiment. Here, the coupling solution 11 is solution including a coupling agent. The immobilization solution 13 is solution including an immobilization agent. The activation solution 15 is solution including an activation agent. Antibody is bound to the coupling agent, the coupling agent is bound to the immobilization agent, the immobilization agent is bound to the activation agent and the activation agent is bound to the cup 5, which leads to the antibody immobilized in the cup 5 as a whole.

In addition, the buffer solution 17 plays a passive role of, in the antibody chip 1, preventing each solution from air and keeping solutions in isolation from each other. On the other hand, the antibody solution 9 and the bond solution 73 that binds the antibody and the cup 5 play an active role. Thus, the antibody solution 9 and the bond solution 73 are called function solution as a collective term below.

Figure 3:
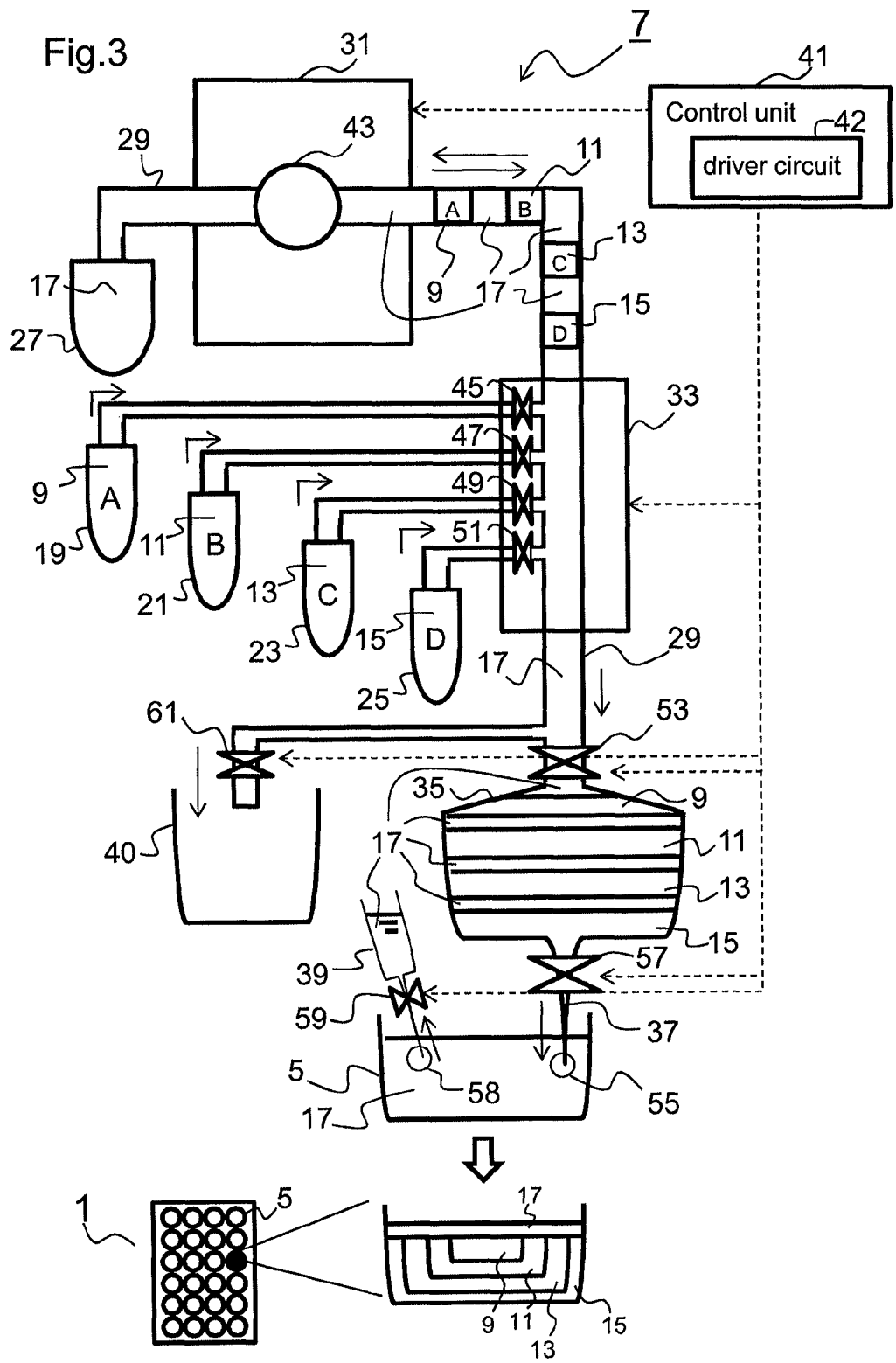
FIG. 3 illustrates an example of a generation device 7 for generating the antibody chip 1 in FIG. 1 in more detail.

Referring to FIGS. 3 through 7, the present embodiment will be described more specifically. FIG. 3 illustrates a generation device 7 for generating the antibody chip 1 in FIG. 1 in more detail.

Referring to FIG. 3, the generation device 7 includes a cup 5 to which antibody is to be bound, an antibody solution holder 19 that holds antibody solution 9, a coupling solution holder 21 that holds coupling solution 11, an immobilization solution holder 23 that holds the immobilization solution 13, an activation solution holder 25 that holds activation solution 15 and a buffer solution holder 27 that holds buffer solution 17. The coupling solution holder 21, the immobilization solution holder 23 and the activation solution holder 25 are examples of "bond solution holder".

The generation device 7 further includes a flow path 29 through which the buffer solution 17 and each function solution flow, a flow controller 31 that controls the flow in the flow path 29, a valve selector 33 that controls the inflows of the function solutions from each of function solution holders 19, 21, 23, or 25 into the flow path 29, an infusion holder 35 that holds the solution to be injected into the cup 5, an injector 37 that injects solution into the cup 5, an ejector 39 that ejects the buffer solution 17 out of the cup 5, a waste collection device 40 that collects waste liquid from the flow path 29, and a control unit 41 that controls various units. The flow path 29, the flow controller 31 and the valve selector 33 as a whole are an example of "transportation unit".

The buffer solution holder 27 is connected to the flow controller 31 via the flow path 29. The antibody solution holder 19, the coupling solution holder 21, the immobilization solution holder 23 and the activation solution holder 25 are connected to the flow path 29 via the valve selector 33. The flow controller 31, the valve selector 33 and the infusion holder 35 are connected in this order via the flow path 29. The solution held by the infusion holder 35 can be flown into the injector 37. The flow path 29 is divided between the valve selector 33 and the infusion 35 and one of the branches is connected to the waste collection device 40 to eject the waste liquid.

The flow controller 31 includes a pump 43 that transports the buffer solution 17 in and out between the buffer solution holder 27 and the flow path 29. The valve selector 33 includes an antibody solution valve 45, a coupling solution valve 47, an immobilization solution valve 49 and an activation solution valve 51 which control the inflows of the antibody solution 9 held in the antibody holder 19, the coupling solution 11 held in the coupling solution holder 21, the immobilization solution 13 held in the immobilization solution holder 23 and the activation solution 15 held in the activation solution holder 25 into the flow path 29, respectively. The infusion holder 35 includes an infusion holder valve 53 that controls the inflow of solution from the flow path 29 into the infusion holder 35. The injector 37 includes an inlet 55 from which solution is injected into the cup 5 and an inlet valve 57 that controls the inflow of solution from the injector 37 into the cup 5. The ejector 39 includes an outlet 58 out of which the buffer solution 17 is ejected from the cup 5 and an ejector valve 59 that controls the outflow of the buffer solution 17 from the cup 5. The waste collection device 40 includes a waste valve 61 that controls the outflow of solution from the flow path 29 into the waste collection device 40.

Figure 4:
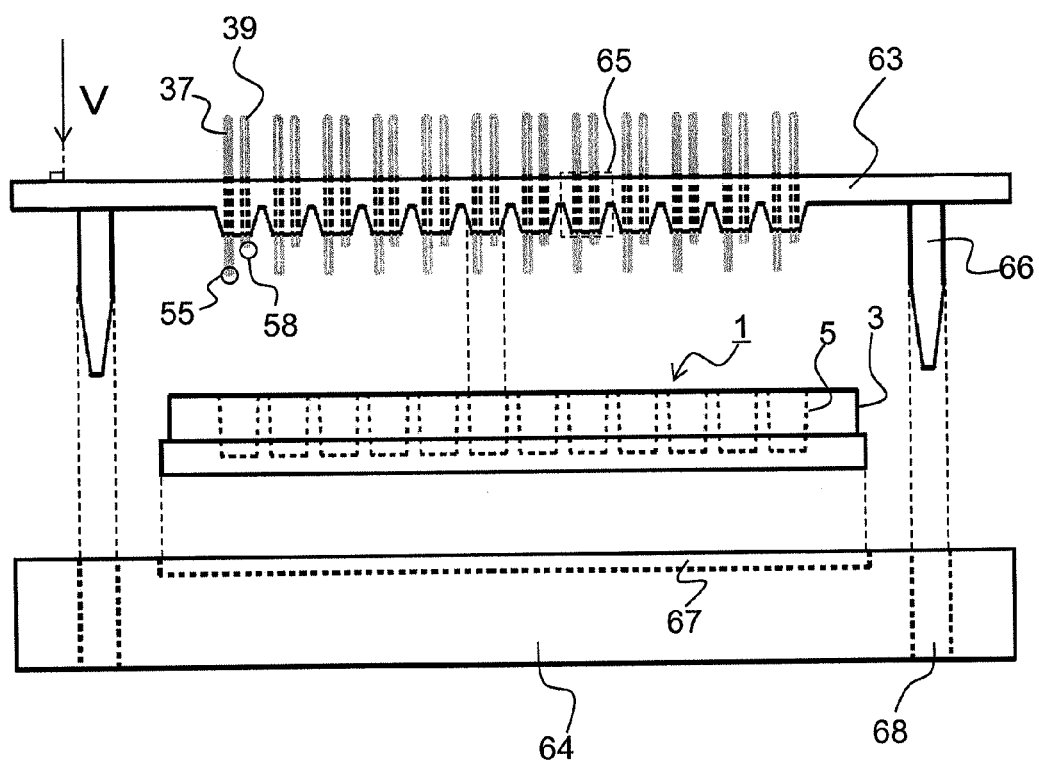
FIG. 4 shows an example of solution adjustment for the antibody chip 1 in FIG. 1.

Here, referring to FIG. 4, the adjustment of solution in a plurality of cups 5 is described. FIG. 4 shows an example of solution adjustment for the antibody chip 1 in FIG. 1.

In order to adjust the solution in the cup 5, a microplate 3 which includes the cup 5 to which antibody is to be bound, a sealing plate 63 (an example of "solution adjuster") for adjusting the solution in the cup 5 and a plate base 64 for securing the microplate 3 to the sealing plate 63 are used.

The sealing plate 63 includes, in each of a plurality of the cups 5, an injector 37 for injecting solution in the infusion holder 35 into the cup 5, an ejector 39 for ejecting the buffer solution 17 in the cup 5, and a sealing 65 (an example of "sealing unit") for sealing the cup 5 keeping a path of injection of solution by the injector 37 and a path of ejection of the buffer solution by the ejector 39. The sealing plate 63 includes a joint member 66 for binding the sealing plate 63, the microplate 3 and the plate base 64. The plate base 64 includes a dent 67 for securing the microplate 3 and a joint hole 68 for joining together with the joint member 66.

The sealing plate 63, the microplate 3 and the plate base 64 are bound by the joint member 66. Then, in each cup 5, the inlet 55 is positioned lower than the outlet 58. This is because the bond solution 73 and the antibody solution 9 should be bound to the cup 5 securely. Besides, the outlets 58 of the cups 5 into which solution is injected at the same time are positioned on the same level. This is because the same amount of buffer solution 17 should be ejected from each of the cups 5 at the same time.

Figure 5:
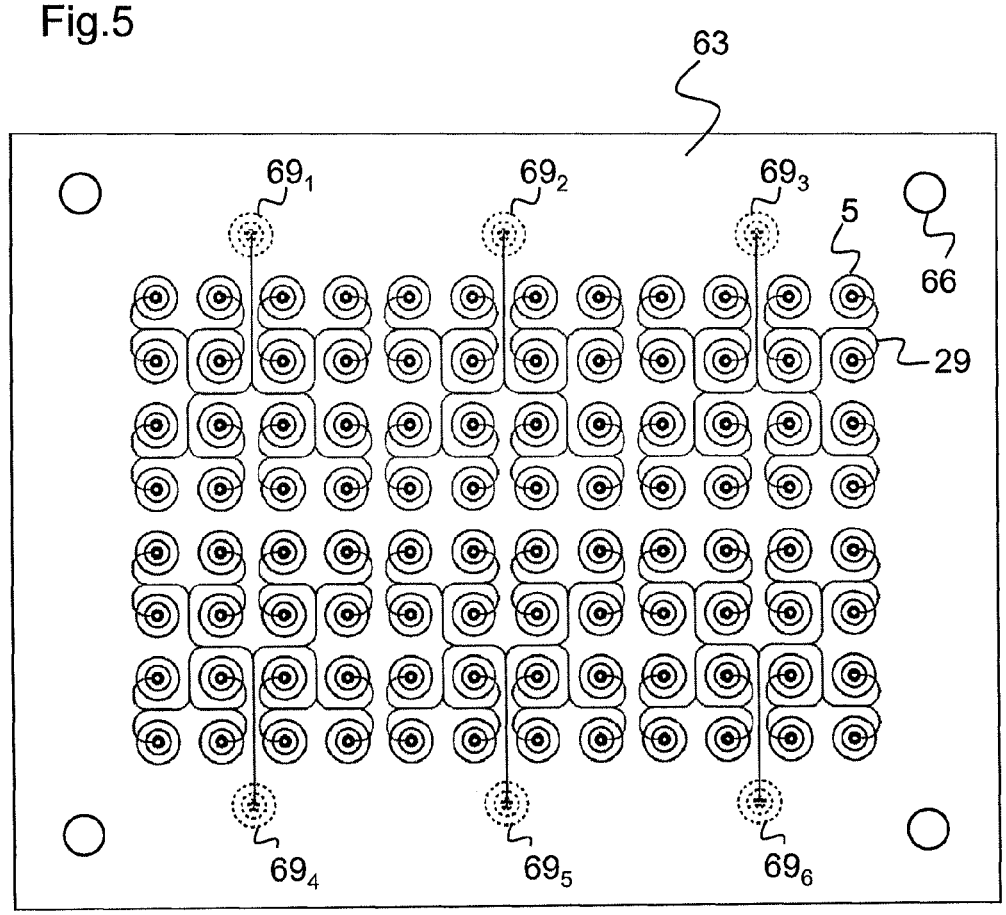
FIG. 5 illustrates an example of the flow path of the antibody chip in FIG. 1.

Further, referring to FIG. 5, the configuration by which the injector 37 injects solution at the same time is described. FIG. 5 illustrates an example of the flow path of the antibody chip in FIG. 1, which is a view of the sealing plate 63 from the direction V vertical to the plane of the plate.

Referring to FIG. 5, the flow path 29 from the infusion holder 35 toward the cups 5 is branched into a plurality of similar flow paths by a branching connector, for example, not illustrated in FIG. 5. Each branched path goes through intermediary holes 69 of the sealing plate 63. Then, from each of the intermediary holes 69 to each of cups 5, the flow paths 29 are further biforked once or more. For example, in FIG. 5, the microplate 3 has 96 cups 5. The flow path 29 out of the infusion holder 35 is first divided into 6 branches which go through 6 intermediary holes from $69_1$ to $69_6$, respectively, further biforked four times after each of the intermediary holes 69, and get to $6 \times 2^4 = 96$ cups 5. Besides, a part of the flow path 29 to each cup 5 forms a fractal figure.

Here, in FIG. 5, only the part of the flow path 29 to the inlet 37 is shown and the part out of the ejector 39 is not shown for sake of simplicity.

As described above, if the flow path 29 is repeatedly biforked to the plurality of cups 5, it is possible to inject the same amount of solution into the plurality of cups 5 at the same time with identical environments of the flow paths 29 out of the infusion holder 35 to each of the inlets 55 such as distance or shape. As a result, the same amount of solution is injected into the plurality of the cups 5 and ejected out of the cups 5 simultaneously, leading to the generation of the antibody chips 1 in which antibody is homogeneously bound to the plurality of the cups 5.

Next, the control of solution transportation by the flow controller 31 is described. The control unit 41 controls the flow controller 31, the valve selector 33, the infusion holder 35, the injector 37, the ejector 39 and the waste collection device 40 to control the flow of solution. In FIG. 3, the antibody solution 9, the coupling solution 11, the immobilization solution 13 and the activation solution 15 are expressed by A, B, C and D, respectively. The control unit 41 controls the flow controller 31 and the valve selector 33 to keep each solution in isolation to each other by the buffer solution 17 in the flow path 29. And the activation solution 15, the immobilization solution 13, the coupling solution 11 and the antibody solution 9 are arranged in the flow path 29 in the ascending order according to the distance to the inlet 55. In the infusion holder 35, too, the solutions are held in the same order according to the distance to the inlet 55 and injected into the cup 5 in the same order by the injector 37.

Here, a driver circuit 42 of the control unit 41 drives a solenoid valve 81 of the valve selector 33. The solenoid valve 81 plays an important role of controlling the inflow of solution into the flow path 29. In general, antibody is sensitive to not only air but also heat. However, driving the solenoid valve 81 needs the voltage above a certain threshold.

The solenoid valve 81 generates heat from power consumption when applying voltage. Thus, it is necessary to reduce the damage of solution such as the antibody solution 9 based on heat generation from the solenoid valve 81 as much as possible. Then, as the solenoid valve 81, a self-sustaining type solenoid valve, which opens or closes when energized and which sustains its switching condition after stopping the energization, is adopted. Because such a solenoid valve can sustain its switching condition after stopping the energization, it is possible to reduce the heat generation from the solenoid valve as much as possible.

An example of the solenoid valve 81 is a latch type solenoid valve. The solenoid valve 81 includes a plunger that opens or closes the valve (not shown in the figure), a solenoid 83 that moves the plunger by the electromagnetic force when energized, a magnet that sustains the position of the plunger after stopping the energization (not shown in the figure), and a spring that prevents the displacement of the plunger from the position before energization by applying force against the displacement direction (not shown in the figure). When the solenoid 83 is energized, the plunger is moved by the electromagnetic force and the valve is opened or closed. The magnet keeps the position of the displaced plunger and the position of the plunger is sustained even after stopping the energization. At this time, the spring is forced to change in shape, storing elastic energy. To put the plunger back in place, the solenoid 83 is energized by the voltage of the inversed polarity. Then, the solenoid 83 generates the magnetic field against the magnet, and the plunger is put back in place by the stored elastic energy of the spring.

Figure 6:
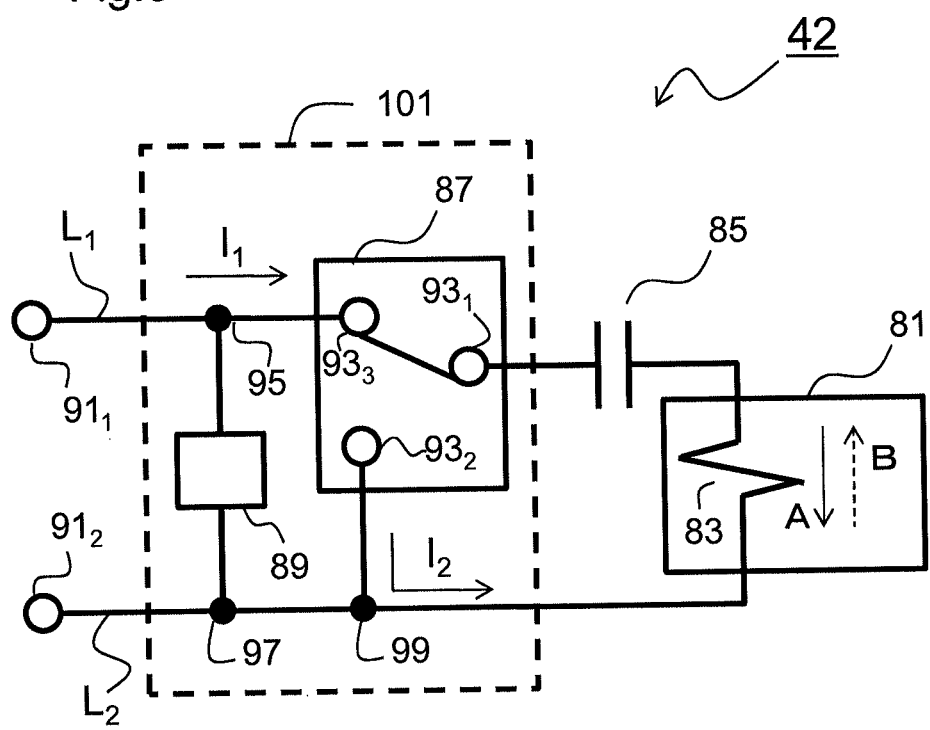
FIG. 6 shows the circuit diagram of the driver circuit 42 in FIG. 3.

Here, the circuit configuration of the driver circuit 42 that drives the solenoid 81 at the lowest voltage is described. FIG. 6 shows the circuit diagram of the driver circuit 42 in FIG. 3.

Referring to FIG. 6, the driver circuit 42 includes the solenoid 83 that opens or closes the solenoid valve 81 by energization, a capacitor 85 that stores electric charge after beginning of the energization on the solenoid 83, a relay 87 that switches connection relation, a magnet coil 89 (an example of "switch unit") that controls the switching of the relay 87, and a first terminal $91_1$ and a second terminal $91_2$ for applying voltage to the magnet coil 89 and to the solenoid 83, the capacitor 85 and the relay 87.

The solenoid valve 81 is opened or closed by electromagnetic power when current flows in the solenoid 83. The opened or closed solenoid valve 81 by electromagnetic power sustains the switching condition after stopping the current to the solenoid 83. As an example, assuming that the solenoid valve 81 is opened when current flows in the direction A expressed by a solid arrow in FIG. 6, the solenoid valve 81 stays open after the current in the direction A vanishes. On the contrary, when the current flows in the direction B expressed by a dashed arrow, the solenoid valve 81 closes and stays closed after the current in the direction B vanishes.

Next, the connection relation of the circuit components in the driver circuit 42 is described. The solenoid 83, the capacitor 85 and the relay 87 are connected sequentially. The magnet coil 89 is connected in parallel with the solenoid 83, the capacitor 85 and the relay 87. The first terminal $91_1$ and the second terminal $91_2$ are connected so as to apply voltage in parallel with the magnet coil 89. The relay 87 includes three contact points (a first contact point $93_1$, a second contact point $93_2$ and a third contact point $93_3$). The first contact point $93_1$ of the relay 87 is connected to the capacitor 85, the second contact point $93_2$ is connected to the solenoid 83 and the magnet coil 89, and the third contact point $93_3$ is connected to the magnet coil 89. A first line $L_1$ is a conducting wire that connects the third contact point $93_3$ of the relay 87 and the first terminal $91_1$. A second line $L_2$ is a conducting wire that connects the solenoid 83 and the second terminal $91_2$. One end of the capacitor 85 is connected to the first contact point $93_1$ of the relay 87 and the other end of the capacitor 85 is connected to the solenoid 83. One end of the solenoid 83 is connected to the capacitor 85 and the other end of the solenoid 83 is connected to the second contact point $93_2$ of the relay 87 and the magnet coil 89. One end of the magnet coil 89 is connected to the first line $L_1$ at a connecting point 95. The other end of the magnet coil 89 is connected to the second line $L_2$ at a connecting point 97. The second contact point $91_2$ of the relay 87 is also connected to the second line $L_2$ at the connecting point 99. The relay 87 and the magnet coil 89 forms an electromagnetic relay 101 as a whole.

The electromagnetic relay 101 is described in more detail. The first contact point $93_1$ of the relay 87 is a common contact point which is connected only any of the second contact point $93_2$ or the third contact point $93_3$. The first contact point $93_1$ is connected to the second contact point $93_2$, a normally closed contact point, when voltage is not applied to the magnet coil 89, and the first contact point $93_1$ is connected to the third contact point $93_3$, a normally open contact point, when voltage is applied to the magnet coil 89.

The behavior of the driver circuit 42 is described below. First, the voltage is not applied between the first terminal $91_1$ and the second terminal $91_2$. Then, the first contact point $93_1$ and the second contact point $93_2$ are connected in the relay 87.

When voltage V is applied between the first terminal $91_1$ and the second terminal $91_2$, the first contact point $93_1$ and the third contact point $93_3$ are connected in the relay 87. Then, the voltage V is applied to the solenoid 83 and current flows in the direction A in FIG. 6, for example. The plunger is displaced by the electromagnetic force and the position of the plunger is self-sustained by the magnet. Accordingly, the voltage is applied to the capacitor 85 and the capacitor 85 begins to store charge. While the capacitor 85 is charged, the current which flows in the solenoid 83 decreases. After charging for the time determined by the time constant of the capacitor 85, the entire voltage V is applied to the capacitor 85 and the solenoid 83 is not energized. Thus, the solenoid valve 81 can sustain the switching condition of the valve without heat generation based on energization. Besides, though the voltage V is applied to the capacitor 85 which stores charge, the power consumption is limited because the current does not flow.

When applying voltage is stopped between the first terminal $91_1$ and the second terminal $91_2$, the first contact point $93_1$ and the second contact point $93_2$ are connected again in the relay 87. Then, the charge stored in the capacitor 85 applies voltage V in the inverse direction (the direction B in FIG. 6) to the solenoid 83. Now, the magnet cannot sustain the plunger against the electromagnetic force by the solenoid 83 plus the force by the spring and the plunger is put back in place. As this, the solenoid valve 81 gets back by discharge of the capacitor 85. The capacitor 85 discharges completely and can afford the next charging.

By utilizing the driver circuit 42, it is possible to control the self-sustaining type solenoid valve 81 with an extremely simple and small circuit. Besides, a user can operate the valve selector 33 without changing the direction of applying voltage to open and close the solenoid valve 81. The user only has to apply voltage V to activate the solenoid valve 81 and stop applying the voltage V to return the solenoid valve 81. As this, by utilizing the driver circuit 42 which realizes the operation with simple correspondence between applying voltage and switching condition of the solenoid valve, it is easier to generate the antibody chip 1 rapidly.

Figure 7:
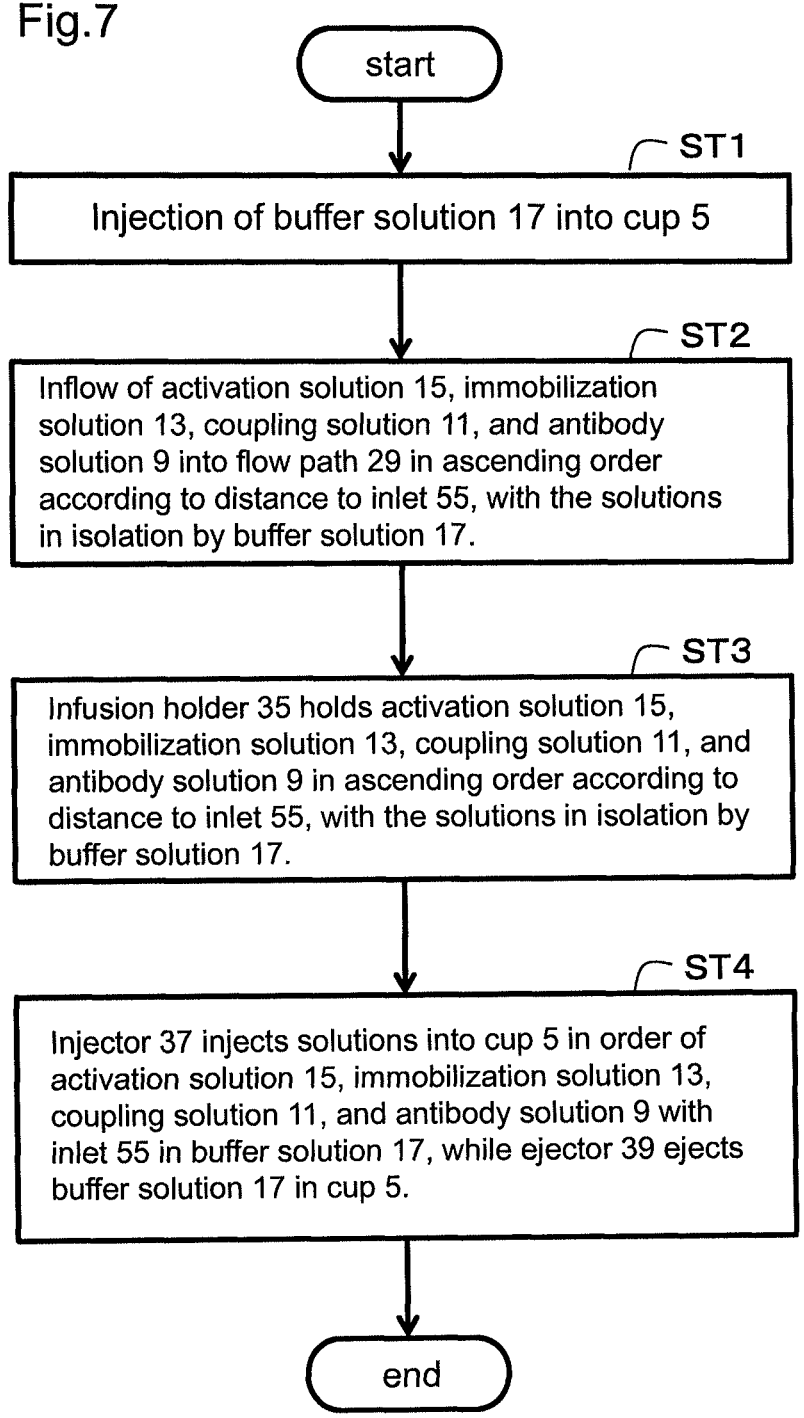
FIG. 7 shows an example of the generation process by the generation device 7 in FIG. 3.
Figure 9:
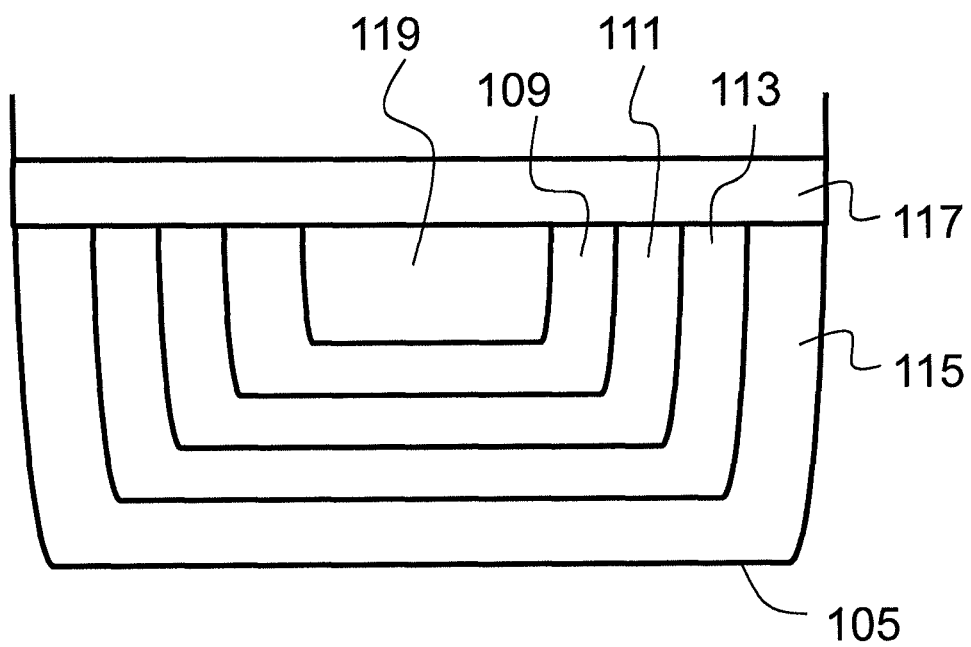
FIG. 9 illustrates a cross-section view of the cup 105 of a conventional antibody chip.
Figure 10:
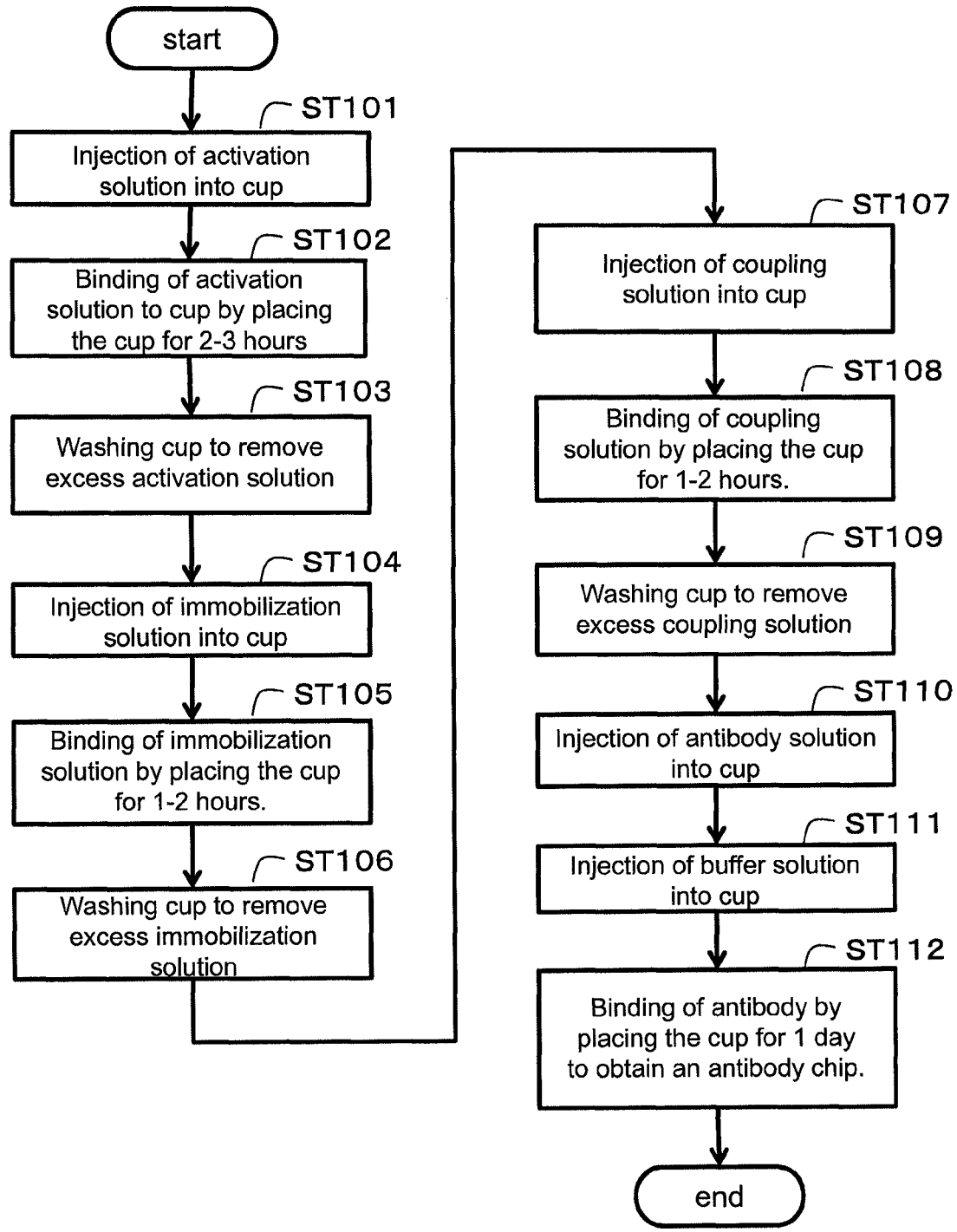
FIG. 10 shows the outline of the generation process of the antibody chip in FIG. 9.

Below, the procedure to immobilize the antibody is described to explain the outline of the generation process of the antibody chip 1 of the embodiment of the present invention. FIG. 7 shows the outline of the generation process for generating the antibody chip 1 of the present embodiment.

Referring to FIG. 7, the injector 37 injects the buffer solution 17 into the cup 5 (step ST1). Then, the control unit 41 controls the flow controller 31 and the valve selector 33 to let the activation solution 15 out of the activation solution holder 25, the immobilization solution 13 out of the immobilization solution holder 23, the coupling solution 11 out of the coupling solution holder 21, and the antibody solution 9 out of the antibody solution holder 19 into the flow path 29. Here, the activation solution 15, the immobilization solution 13, the coupling solution 11, and the antibody solution 9 in the ascending order according to the distance to the inlet 55 are let into the flow path 29 with every solution in isolation to each other by the buffer solution 17 (step ST2). Further, the control unit 41 controls the infusion holder 35 to let the activation solution 15, the immobilization solution 13, the coupling solution 11, and the antibody solution 9 out of the flow path 29 into the infusion holder 35 and to hold the solution let in. Here, the control unit 41 controls the infusion holder 35 to hold the activation solution 15, the immobilization solution 13, the coupling solution 11, and the antibody solution 9 in the ascending order according to the distance to the inlet 55 with every solution in isolation to each other by the buffer solution 17 (step ST3). Next, the control unit 41 controls the injector 37 and the ejector 39 to inject the solution from the injector 37 with the inlet 55 in the buffer solution 17 in the cup 5 (step ST4). Here, because the ejector 39 ejects the buffer solution 17 as necessary, the buffer solution 17 does not overflow out of the cup 5. In addition, the injector 37 injects the solution so that the layers of the activation solution 15, the immobilization solution 13, the coupling solution 11, and the antibody solution 9 in the ascending order according to the distance to the cup 5 are formed in the cup 5.

The waste collection device 40 collects the solution out of the flow path 29 as unnecessary waste liquid, while, for example, the infusion holder 35 does not let solution in.

The generation device 7 automatically transports each solution from each of the solution holders 17, 19, 21, 23, and 25 into the injector 37 without exposure of each solution to air. Further, by injecting the buffer solution 17 in the cup 5 in advance, it is possible to generate the antibody chip 1 without exposure to air. The completed antibody chip 1 is, unlike a conventional antibody chip, not exposed to air. Therefore, it is possible to have the antibody chip 1 in stock for a long time. The applicant demonstrated that the generated antibody chip 1 by the present invention could be cured for more than half a year. Thus, it is possible to have the antibody chip 1 in stock to execute a rapid examination when necessary in the field such as hospitals, food manufacturers, and so on.

Further, it is possible to eliminate the need for the procedures of placing still and the procedures of washing in the generation process of the antibody chip 1. Therefore, it is possible to generate the antibody chips 1 at low price for a short time, resulting in drastic cost reduction.

Further, because the ejector 39 ejects the buffer solution 17 as necessary, it is possible to generate an antibody chip without the overflow of the buffer solution out of the cup. Therefore, by equipping each cup 5 with the injector 37 and the ejector 39 and by injecting and ejecting solution simultaneously in a plurality of cups 5, it is possible to generate the antibody chip 1 with a plurality of cups 5 condensed in the microplate 3 as shown in FIG. 1 for a short time.

Here, as long as the buffer solution 17 is in the cup before the function solution is injected into the cup 5, the order of step ST1 and the step ST2 in the embodiment may be inversed. In addition, in the step ST3, if the infusion holder 35 holds the buffer solution 17 nearer to the inlet 55 than the activation solution 15, the step ST1 of the embodiment maybe after the step ST3. Further, it is favorable to fill the cup 5 with the buffer solution 17 in advance to prevent the function solution from the exposure to air. However, if the inlet 55 is in the buffer solution 17 in the cup 5 during injection of the function solution, the cup 5 may not be full of the buffer solution 17 in advance.

In addition, as long as the bond solution layer 72 is formed, in the cup 5 of FIG. 2, between the antibody solution 9 and the cup 5, it does not matter whether the bond solution 73 is held in the infusion holder 35 before or after the antibody solution 9 is held. For example, as long as the layer of the bond solution 73 is formed between the antibody solution 9 and the cup 5, the bond solution 73, the buffer solution 17 and the antibody solution 9 in this order may be injected from the top of the infusion holder 35 and held inside. Or, the antibody solution 9, the buffer solution 17 and the bond solution 73 in this order may be aspirated from the inlet 55 into the infusion holder 35 and held inside.

Further, in FIG. 3, the antibody solution 9, the coupling solution 11, the immobilization solution 13 and the activation solution 15 of the antibody chip 1 only have to be arranged in the cup 5 in the order that the antibody is bound to the cup 5. FIG. 8 illustrates the examples of distribution of solutions when the antibody solution 9, the coupling solution 11, the immobilization solution 13 and the activation solution 15 are injected into the cup 5. The layers of solutions may be stacked in parallel to the horizontal plane of the layer of the buffer solution 17 (FIG. 8(a)). The layers of solutions may be wavy (FIG. 8 (b)). Or the layers of solutions may be stacked vertically to the layer of the buffer solution 17 (FIG. 8(c)).

Further, as long as the coupling solution 11, the immobilization solution 13 and the activation solution 15 are as a whole the solution for binding antibody to the cup 5, the solutions may be discretely different or a single solution as the bond solution 73. In addition, the antibody solution 9 may include a plurality of kinds of antibody.

Further, the antibody solution 9, the coupling solution 11, the immobilization solution 13, the activation solution 15, the buffer solution 17 or the bond solution 73 may be, as long as they bind antibody to the cup as a whole, sol or gel. Here, if gas is included in solution, in particular in the antibody solution 9, it is favorable to include inactive gas such as nitrogen not to shorten the life-span of the antibody.

Further, if it is possible to transport each solution without exposure to air by, for example, executing the procedures under a special environment such as under nitrogen atmosphere, a part of the procedures may be executed by hand.

Further, in FIG. 4, when binding the sealing plate 63, the microplate 3 and the plate base 64, it is favorable to bind them while fixing the sealing plate 63. This is because the inlets 55 and the outlets 58 should be kept on the same level in height. By this, it is easier to produce the antibody chips 1 rapidly in large volume exchanging the microplate 3.

Further, in FIG. 5, the flow path 29 may be fixed in the sealing plate 63 or not. For example, the entire flow path 29 maybe fixed by being embedded in the sealing plate 63 or by being bound between the sealing plate and another plate. Or only a part of the flow path 29 may be fixed in the sealing plate 63.

Further, in FIG. 6, if the solenoid 83, the capacitor 85 and the relay 87, the magnet coil 89 that controls the relay 87, and the first terminal $91_1$ and the second terminal $91_2$ for applying voltage are connected in parallel, the connecting point 95 may not necessarily on the first line $L_1$. Similarly, the connecting point 97 and the connecting point 99 may not necessarily on the second line $L_2$.

In addition, if the first contact point $93_1$ of the relay 87 is connected to the third contact point $93_3$ when voltage is applied and if the first contact point $93_1$ is connected to the second contact point $93_2$ when the voltage is stopped, the first contact $93_1$ maybe connected to the third contact point $93_3$ while voltage is not applied after the charge stored in the capacitor 85 is completely discharged.

Further, if the solenoid valve 81 is a self-sustaining type solenoid valve which opens or closes when voltage is applied to the solenoid 83 for reducing heat generation, the solenoid valve 81 may be a valve other than latch type solenoid valve.

Reference Signs List

1 Antibody chip, 5 Cup, 7 Generation device, 9 Antibody solution, 17 Buffer solution, 19 Antibody solution holder, 27 Buffer solution holder, 29 Flow path, 33 Valve selector, 35 Infusion holder, 37 Injector, 39 Ejector, 41 Control unit, 42 Driver circuit, 55 Inlet, 58 Outlet, 65 Sealing, 81 Solenoid valve

The invention claimed is:

1. A generation device for generating an antibody chip by binding antibody to a cup, comprising:
   the cup;
   a buffer solution holder holding a buffer solution;
   an antibody solution holder holding an antibody solution having the antibody;
   an infusion holder configured to hold an infusion comprising the buffer solution and the antibody solution, the infusion holder being connected to the buffer solution holder and the antibody solution holder without exposure of the buffer solution and the antibody solution to air;
   a solution adjuster that adjusts solution in the cup, the solution adjuster being connected to the infusion holder without exposure of the infusion to air;
   control unit that controls the infusion holder and the solution adjuster; and
   a bond solution holder holding a bond solution for binding the antibody and the cup, the bond solution holder being connected to the infusion holder without exposure of the bond solution to air,
   wherein the solution adjuster includes an injector comprising an inlet from which the buffer solution and the antibody solution are injected into the cup, and an ejector comprising an outlet out of which the buffer solution is ejected from the cup;
   the infusion holder contains the antibody solution, the buffer solution, and the bond solution; wherein the buffer solution isolates the bond solution from the antibody solution; and
   the injector injects the bond solution, the buffer solution, and the antibody solution held by the infusion holder through the inlet and into the cup.

2. The generation device of claim 1, wherein the infusion holder contains the bond solution constituting a first layer, the buffer solution constituting a second layer next to the first layer and the antibody solution constituting a third layer next to the second layer in ascending order according to distance to the inlet so that the injector injects the bond solution, the buffer solution and the antibody solution into the cup and layers of the bond solution and the antibody solution are formed in order of injection in the cup.

3. The generation device of claim 1, further comprising a transportation unit that transports the antibody solution from the antibody solution holder to the injector, wherein the transportation unit includes a valve selector that controls inflow of the antibody solution to a flow path through which the antibody solution is transported; and the valve selector includes a solenoid valve that switches a valve by energization and keeps a switching condition without the energization.

4. The generation device of claim 3, further comprising a driver circuit that drives the solenoid valve, wherein the driver circuit includes:

a solenoid that activates the solenoid valve by energization;

a capacitor that stores a charge at the beginning of the energization;

a relay that switches connection relation; and a switch unit that controls switching the connection relation by the relay;

the solenoid, the capacitor and the relay are sequentially connected;

the switch unit is connected in parallel with the solenoid, the capacitor and the relay;

the relay permits the energization to the solenoid at the beginning of the energization by allowing application of voltage parallel to the switch unit; and the relay switches the connection relation upon stoppage of the application of the voltage so that the solenoid, the capacitor and the relay forms a closed circuit which does not include the switch unit.

* * * * *